(12) United States Patent
Lueder et al.

(10) Patent No.: US 6,288,021 B1
(45) Date of Patent: *Sep. 11, 2001

(54) METHOD FOR THE PRODUCTION OF WATERFREE AND DUSTFREE ANIONIC SURFACTANTS

(75) Inventors: Thomas Lueder, Langenfeld; Bernd Fabry, Korschenbroich; Joerg Kahre, Leichlingen; Werner Seipel, Hilden, all of (DE)

(73) Assignee: Cognis Deutschland GmbH, Duesseldorf (DE)

(*) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/269,102
(22) PCT Filed: Sep. 29, 1997
(86) PCT No.: PCT/EP97/05348
§ 371 Date: Mar. 19, 1999
§ 102(e) Date: Mar. 19, 1999
(87) PCT Pub. No.: WO98/15611
PCT Pub. Date: Apr. 16, 1998

(30) Foreign Application Priority Data
Oct. 7, 1996 (DE) ............................................. 196 41 275

(51) Int. Cl.⁷ .................................................. C11D 17/06
(52) U.S. Cl. ........................ 510/445; 510/446; 510/457
(58) Field of Search ..................... 510/457, 446, 510/445

(56) References Cited

U.S. PATENT DOCUMENTS

| | | |
|---|---|---|
| 1,985,424 | 12/1934 | Piggott . |
| 2,016,962 | 10/1935 | Flint et al. . |
| 2,703,798 | 3/1955 | Schwartz . |
| 5,312,932 | 5/1994 | Behler et al. . |
| 5,322,957 | 6/1994 | Fabry et al. . |
| 5,374,716 | 12/1994 | Biermann et al. . |
| 5,397,507 * | 3/1995 | Bauer et al. .......................... 252/549 |
| 5,484,531 | 1/1996 | Kuehne et al. . |
| 5,536,431 | 7/1996 | Carduck et al. . |
| 5,576,425 | 11/1996 | Hill et al. . |

FOREIGN PATENT DOCUMENTS

| | | |
|---|---|---|
| 9669874 | 1/1998 | (AU) . |
| 7 25 474 | 9/1942 | (DE) . |
| 42 04 700 | 8/1993 | (DE) . |
| 42 09 339 | 9/1993 | (DE) . |
| 195 34 371 | 2/1997 | (DE) . |
| 0 301 298 | 2/1989 | (EP) . |
| 0 384 480 | 8/1990 | (EP) . |
| 0 561 825 | 9/1993 | (EP) . |
| 0 561 999 | 9/1993 | (EP) . |
| 0 572 957 | 12/1993 | (EP) . |
| 8-170093 | 7/1996 | (JP) . |
| WO 90/03977 | 4/1990 | (WO) . |
| WO 92/06984 | 4/1992 | (WO) . |
| WO 93/19155 | 9/1993 | (WO) . |

OTHER PUBLICATIONS

Database WPI, Derwent Publications Ltd., Class D25, An–96–358656, XP002058428.
A. Biswas, B. Mukherji, "Surface–Active Properties of Sodium Salts of Sulfated Fatty Acid Monoglycerides", J. Am. Oil. Soc.37 (1960) pp. 171–175.
F. Ahmed, "Efficient Synthesis of Fatty Monoglyceride Sulfates from Fatty Acids and Fatty Acid Methyl Esters", J. Am. Oil. Soc. 67,8 (1990) pp. 8–14.
"Detergenzien auf Zuckerbasis", Tenside Surfactants Detergents 25 (1988) pp. 8–13.

* cited by examiner

Primary Examiner—Scott W. Houtteman
(74) Attorney, Agent, or Firm—John E. Drach; Steven J. Trzaska

(57) ABSTRACT

A process for making substantially water- and dust-free anionic surfactant granules of high bulk density involving: (a) providing a starting material containing a water-containing paste of a monoglyceride (ether) sulfate having a solids content of at least 20% by weight, based on the weight of the paste; (b) providing a horizontally mounted thin-layer evaporator with rotating internals; (c) providing a negative temperature gradient within the evaporator; (d) passing air into the evaporator in countercurrent to the flow of starting material; and (e) simultaneously drying and granulating the starting material by passing it through the evaporator to form anionic surfactant granules having a residual water content of below 2% by weight.

20 Claims, No Drawings

METHOD FOR THE PRODUCTION OF WATERFREE AND DUSTFREE ANIONIC SURFACTANTS

BACKGROUND OF THE INVENTION

This invention relates to a process for the simultaneous drying and granulation of water-containing monoglyceride (ether) sulfate pastes using a thin-layer evaporator.

Monoglyceride (ether) sulfates are distinguished by excellent detergent properties and high ecotoxicological compatibility. For this reason, these anionic surfactants are acquiring increasing significance. Although, hitherto, they have generally been used in liquid formulations, for example dishwashing detergents or hair shampoos, there has also been a market demand in the meantime for solid water-free formulations which can be incorporated, for example, in washing powders, toothpastes or syndet soaps.

On an industrial scale, liquid surfactant formulations are generally dried by conventional spray drying where the aqueous surfactant paste is sprayed at the head of a tower in the form of fine droplets which meet hot drying gases flowing in countercurrent. However, the drastic conditions involved often lead to hydrolysis phenomena, unwanted discoloration of the products, deposits on the walls of the spray drying towers and, hence, to impurities in the spray-dried material in the form of carbonized residues. In addition, the necessary cleaning of the towers results in down times which occasionally make the process expensive. Another problem is that conventional processes do not lead to the particularly preferred heavy powders with a bulk density above 500 g/l and, at the same time, a greatly reduced dust content. However, it is precisely these two parameters which are of considerable importance for economic, performance and safety reasons.

DE-A1 42 09 339 (Henkel) describes a process a process for the production of free-flowing detergent granules in which drying is carried out in turbo dryers, i.e. in horizontally mounted cylindrical dryers with rotating internals. Detergent pastes containing monoglyceride sulfates can also be dried in this way. In addition, powder-form monoglyceride sulfates are also mentioned in DE-PS 725 474.

Accordingly, the complex problem addressed by the present invention was to convert water-containing monoglyceride (ether) sulfate pastes with minimal outlay on equipment and without using inorganic or organic carriers into substantially water-free and dust-free granules which would be distinguished by acceptable color quality, a high bulk density, good flow properties, satisfactory stability in storage and, in comparison with known products, by at least comparable performance properties.

DESCRIPTION OF THE INVENTION

The present invention relates to a process for the production of water-free and dust-free anionic surfactant granules of high bulk density, in which water-containing pastes of monoglyceride (ether)sulfates with a solids content of at least 20% by weight and preferably in the range from 25 to 75% by weight are simultaneously dried to a residual water content below 2% by weight, preferably below 1.5% by weight and more preferably below 1% by weight and converted into particulate form in a horizontally mounted thin-layer evaporator with rotating internals, a negative temperature gradient being applied to the thin-layer evaporator from the product entrance to the product exit, air being passed through the evaporator in countercurrent and drying taking place exclusively via the heated wall.

It has surprisingly been found that a horizontally mounted thin-layer evaporator is ideally suitable for converting water-containing monoglyceride (ether)sulfate pastes into dry, light-colored, free-flowing non-tacky granules without discoloration of the product or caking on the walls. The products have a high bulk density of 550 to 650 g/l and a mean particle diameter of 2.0 to 2.8 mm which leads to a reduction in unwanted water absorption and agglomeration of the particles. High stability in storage is also achieved in this way. At the same time, the particles are dust-free, i.e. the percentage of particles smaller than 200 $\mu$m in diameter is less than 5% by weight. This is all the more surprising insofar as, although equipment of the type mentioned is basically suitable for drying useful materials, the resulting powders do not satisfy the requirements mentioned either in regard to bulk density or in regard to their dust and residual water contents. One particular embodiment of the invention is characterized by the use of mixtures of monoglyceride (ether)sulfates and alkyl and/or alkenyl oligoglycosides and/or fatty acid-N-alkyl glucamides.

Monoglyceride (ether)sulfates

Monoglyceride sulfates and monoglyceride ether sulfates are known anionic surfactants which may be obtained by the relevant methods of preparative organic chemistry. They are normally produced from triglycerides which, optionally after ethoxylation, are transesterified to the monoglycerides and then sulfated and neutralized. The partial glycerides can also be reacted with suitable sulfating agents, preferably gaseous sulfur trioxide or chlorosulfonic acid [cf. EP-B1 0 561 825, EP-B1 0 561 999 (Henkel)]. If desired, the neutralized products may be subjected to ultrafiltration to reduce their electrolyte content to the required level. [DE-A1 42 04 700 (Henkal)]. Overviews of the chemistry of monoglyceride sulfates have been published, for example, by A.K. Biswas et al. In J. Am. Oil. Chem. Soc. 37, 171 (1960) and F. Ahmed in J. Am. Oil. Chem. Soc. 67, 8 (1990). The monoglyceride (ether)sulfates suitable for use in accordance with the invention correspond to formula (I):

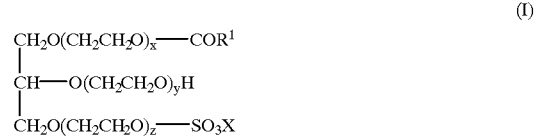

(I)

In which $R^1CO$ is a linear or branched acyl group containing 6 to 22 carbon atoms, x, y and z together stand for 0 or for numbers of 1 to 30, preferably 2 to 10, and X is an alkali metal or alkaline earth metal. Typical examples of monoglyceride (ether)sulfates suitable for the purposes of the invention are the reaction products of lauric acid monoglyceride, cocofatty acid monoglyceride, palmitic acid monoglyceride, stearic acid monoglyceride, oleic acid monoglyceride and tallow fatty acid monoglyceride and ethylene oxide adducts thereof with sulfur trioxide or chlorosulfonic acid in the form of their sodium salts. Monoglyceride sulfates corresponding to formula (I) in which $R^1CO$ is a linear acyl group containing 8 to 18 carbon atoms are preferably used.

Alkyl and/or alkenyl oligoglycosides

Alkyl and alkenyl oligoglycosides are known nonionic surfactants corresponding to formula (II):

$$R_2O\text{---}[G]_p \quad \text{(II)}$$

in which $R^2$ is an alkyl and/or alkenyl radical containing 4 to 22 carbon atoms, G is a sugar unit containing 5 or 6 carbon atoms and p is a number of 1 to 10. They may be obtained by the relevant methods of preparative organic chemistry. EP-A1 0 301 298 and WO 90/03977 are cited as representative of the extensive literature available on the subject. The alkyl and/or alkenyl oligoglycosides may be derived from aldoses or ketoses containing 5 or 6 carbon atoms, preferably glucose. Accordingly, the preferred alkyl and/or alkenyl oligoglycosides are alkyl and/or alkenyl oligoglucosides. The index p in general formula (II) indicates the degree of oligomerization (DP), i.e. the distribution of mono- and oligoglycosides, and is a number of 1 to 10. Whereas p in a given compound must always be an integer and, above all, may assume a value of 1 to 6, the value p for a certain alkyl oligoglycoside is an analytically determined calculated quantity which is generally a broken number. Alkyl and/or alkenyl oligoglycosides having an average degree of oligomerization p of 1.1 to 3.0 are preferably used. Alkyl and/or alkenyl oligoglycosides having a degree of oligomerization of less than 1.7 and, more particularly, between 1.2 and 1.4 are preferred from the applicational point of view.

The alkyl or alkenyl radical $R^2$ may be derived from primary alcohols containing 4 to 11 and preferably 8 to 10 carbon atoms. Typical examples are butanol, caproic alcohol, caprylic alcohol, capric alcohol and undecyl alcohol and the technical mixtures thereof obtained, for example, in the hydrogenation of technical fatty acid methyl esters or in the hydrogenation of aldehydes from Roelen's oxosynthesis. Alkyl oligoglucosides having a chain length of $C_8$ to $C_{10}$ (DP=1 to 3), which are obtained as first runnings in the separation of technical $C_{8-18}$ coconut oil fatty alcohol by distillation and which may contain less than 6% by weight of $C_{12}$ alcohol as an impurity, and also alkyl oligoglucosides based on technical $C_{9/11}$ oxoalcohols (DP=1 to 3) are preferred. In addition, the alkyl or alkenyl radical $R^2$ may also be derived from primary alcohols containing 12 to 22 and preferably 12 to 14 carbon atoms. Typical examples are lauryl alcohol, myristyl alcohol, cetyl alcohol, palmitoleyl alcohol, stearyl alcohol, isostearyl alcohol, oleyl alcohol, elaidyl alcohol, petroselinyl alcohol, arachyl alcohol, gadoleyl alcohol, behenyl alcohol, erucyl alcohol, brassidyl alcohol and technical mixtures thereof which may be obtained as described above. Alkyl oligoglucosides based on hydrogenated $C_{12/14}$coco alcohol with a DP of 1 to 3 are preferred.

Fatty acid N-alkyl polyhydroxyalkylamides

Fatty acid N-alkyl polyhydroxyalkylamides are nonionic surfactants which correspond to formula (III):

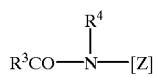

(III)

where $R^3CO$ is an aliphatic acyl radical containing 6 to 22 carbon atoms, $R^4$ is hydrogen, an alkyl or hydroxyalkyl radical containing 1 to 4 carbon atoms and [Z] is a linear or branched polyhydroxyalkyl radical containing 3 to 12 carbon atoms and 3 to 10 hydroxyl groups.

The fatty acid N-alkyl polyhydroxyalkylamides are known compounds which may normally be obtained by reductive amination of a reducing sugar with ammonia, an alkylamine or an alkanolamine and subsequent acylation with a fatty acid, a fatty acid alkyl ester or a fatty acid chloride. Processes for their production are described in U.S. Pat. No. 1,985,424, in U.S. Pat. No. 2,016,962 and in U.S. Pat. No. 2,703,798 and in International patent application WO 92/06984. An overview of this subject by H. Kelkenberg can be found in Tens. Surf. Det. 25, 8 (1988). The fatty acid N-alkyl polyhydroxyalkylamides are preferably derived from reducing sugars containing 5 or 6 carbon atoms, more particularly from glucose. Accordingly, the preferred fatty acid N-alkyl polyhydroxyalkylamides are fatty acid N-alkyl glucamides which correspond to formula (IV):

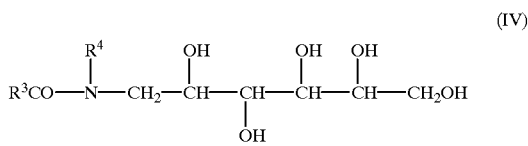

(IV)

Preferred fatty acid N-alkyl polyhydroxyalkylamides are glucamides corresponding to formula (IV) in which $R^4$ is an alkyl group and $R^3CO$ represents the acyl component of caproic acid, caprylic acid, capric acid, lauric acid, myristic acid, palmitic acid, palmitoleic acid, stearic acid, isostearic acid, oleic acid, elaidic acid, petroselic acid, linoleic acid, linolenic acid, arachic acid, gadoleic acid, behenic acid or erucic acid or technical mixtures thereof. Fatty acid N-alkyl glucamides (IV) obtained by reductive amination of glucose with methylamine and subsequent acylation with lauric acid or $C_{12/14}$coconut oil fatty acid or a corresponding derivative are particularly preferred. In addition, the polyhydroxyalkylamides may also be derived from maltose and palatinose.

Drying and granulation in a flash dryer

The simultaneous drying and granulation process takes place in a horizontally mounted thin-layer evaporator with rotating internals, for example of the type marketed by VRV S.p.A. of Milan under the name of "Flash Dryer". In simple terms, this is a tube which can be heated to different temperatures over several zones. The paste-form starting material introduced by a pump is projected against the heated wall via one or more shafts equipped with paddles or plowshares as rotating internals and is dried on the heated wall in a thin layer typically between one and 10 mm in thickness. According to the invention, it has proved to be of advantage to apply a temperature gradient from 170° C. (product entrance) to 20° C. (product exit) to the thin-layer evaporator. This may be done, for example, by heating the first two zones of the evaporator to 160° C. and cooling the last zone to 20° C. Where sugar surfactants are used as further starting materials, higher drying temperatures have proved to be of no advantage in view of the thermal lability. The thin-layer evaporator is operated at atmospheric pressure with air flowing in countercurrent (throughput 50 to 150 m³/h). The entry temperature of the gas is generally from 20 to 30° C. while its exit temperature is in the range from 90 to 110° C. The water-containing monoglyceride (ether) sulfate pastes suitable for use as starting materials may have a solids content above 20% by weight and preferably in the range from 25 to 75% by weight. Their solids content is typically in the range from 30 to 50% by weight. The throughput is of course dependent upon the size of the dryer, but is typically between 5 and 15 kg/h. It is advisable to heat the pastes to 40–60° C. during their introduction. After drying, it has proved to be of considerable advantage to transfer the granules, which still have a temperature of about 50 to 70° C., to a conveyor belt, preferably a vibrating shaft, where they are rapidly cooled, i.e. in 20 to 60 seconds, with ambient air to temperatures of about 30 to 40° C. In order further to improve resistance to unwanted water absorption, the granules may also be subsequently "powdered" by addition of 0.5 to 2% by weight of silica.

Commercial Applications

The granules obtainable by the process according to the invention may be subsequently mixed with other ingredients of powder-form surface-active products, for example tower powders for detergents. The powders may also be readily incorporated in aqueous formulations. In fact, it has been found that there are no differences in performance where the powders are used as opposed to the water-containing starting pastes. The granules may readily be incorporated in bar soaps of the combination bar or syndet type, for example together with fatty acids, fatty acid salts, fatty alcohols, starch, polyglycols and the like.

EXAMPLES

Example 1

The granules were produced in a VRV flash dryer. This is a horizontally mounted thin-layer evaporator (length 1100 mm, internal diameter 155 mm) with 4 shafts and 22 paddles arranged at a distance of 2 mm from the wall. The dryer had three separate heating or cooling zones and a total heat exchange surface of 0.4 $mm^2$ and was operated under normal pressure. A water-containing paste of a cocofatty acid monoglyceride sulfate sodium salt (Plantopon® CMGS, solids content ca. 50% by weight) heated to 50° C. was pumped by a vibrating pump (throughput 11.5 kg/h) into the thin-layer evaporator of which the heating zones 1 and 2 had been adjusted to 160° C. and the cooling zone 3 to 20° C. The speed of the rotors was 24 m/s. Air was passed through the flash dryer (ca. 110 $m^3$/h); the gas exit temperature was ca. 65° C. The predried granules, which still had a temperature of about 60° C., were introduced into a vibrating chute (length 1 m) and cooled with ambient air to about 40° C. in 30 seconds. The granules were then powdered with about 1% by weight of silica (Sipernat® 50 S). The granules obtained were dry and pure white in color and, even after prolonged storage in air, flowed freely and did not agglomerate. After incorporation in shampoo formulations, the granules behaved no differently from a paste-form comparison product. The characteristic data of the granules are set out in Table 1 below:

TABLE 1

Characteristic data of the flash dryer granules

| Parameter | Granules |
|---|---|
| Particle size distribution [% by weight] | |
| <1.0 mm | 1.0 |
| 1.0 mm | 47.2 |
| 2.5 mm | 17.1 |
| 3.2 mm | 17.3 |
| 4.0 mm | 10.3 |
| 5.0 mm | 5.1 |
| 6.2 mm | 2.0 |
| Residual water content (Fischer) [% by weight] | 0.9 |
| Bulk density [g/l] | 610 |

Example 2

Example 1 was repeated with a mixture of 60% by weight of cocofatty acid monoglyceride sulfate and 40% by weight of cocoalkyl oligoglucoside (Plantacare® APG 1200). The temperature in the two heating zones of the flash dryer was increased to 170° C. The granules obtained were again pure white in color, flowed freely with no tendency to agglomerate and had a bulk density of 600 g/l and a residual water content of 0.8% by weight.

Example 3

Example 1 was repeated with a mixture of 60% by weight of cocofatty acid monoglyceride sulfate and 40% by weight of cocofatty alcohol (Lanette® O, Henkel KGaA). The temperature in the two heating zones of the flash dryer was increased to 170° C. The granules obtained were again pure white in color, flowed freely with no tendency to agglomerate and had a bulk density of 590 g/l and a residual water content of 0.7% by weight.

Example 4

Example 1 was repeated with a mixture of 60% by weight of cocofatty acid monoglyceride sulfate and 40% by weight of palm kernel oil fatty acid (Edenor PK®, Henkel KGaA). The temperature in the two heating zones of the flash dryer was increased to 170° C. The granules obtained were again pure white in color, flowed freely with no tendency to agglomerate and had a bulk density of 580 g/l and a residual water content of 0.9% by weight.

What is claimed is:

1. A process for making substantially water- and dust-free anionic surfactant granules of high bulk density comprising:

(a) providing a starting material comprising a water-containing paste of a monoglyceride (ether) sulfate having a solids content of at least 20% by weight, based on the weight of the paste;

(b) providing a horizontally mounted thin-layer evaporator with rotating internals having an entrance opening located at one end of the evaporator and an exit opening located at an opposite end of the evaporator;

(c) providing a negative temperature gradient within the evaporator between the entrance opening through which the starting material is introduced into the thin-layer evaporator, and the exit opening through which the granules are emitted;

(d) passing air into the evaporator in countercurrent to the flow of starting material; and (e) simultaneously drying and granulating the starting material by passing it through the evaporator to form anionic surfactant granules having a residual water content of below 2% by weight.

2. The process of claim 1 wherein the monoglyceride (ether) sulfate component corresponds to formula (I):

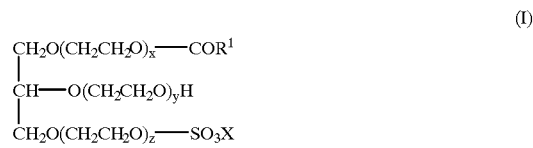

wherein $R^1CO$ is a linear or branched acyl group containing from 6 to 22 carbon atoms, x, y and z represent either 0 or a number from 1 to 30 and X is an alkali metal or alkaline earth metal.

3. The process of claim 1 wherein the starting material further comprises a sugar surfactant selected from the group consisting of an alkyl and alkenyl oligoglycoside corresponding to formula (II):

 (II)

wherein R² is an alkyl and/or alkenyl radical containing from 4 to 22 carbon atoms, G is a sugar unit containing 5 or 6 carbon atoms, and p is a number from 1 to 10, a fatty acid N-alkyl polyhydroxyalkylamide corresponding to formula (III):

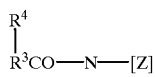 (III)

wherein R³CO is an aliphatic acyl radical having from 6 to 22 carbon atoms, R⁴ is hydrogen, an alkyl or hydroxyalkyl radical containing from 1 to 4 carbon atoms and is [Z] a linear or branched polyhydroxyalkyl radical containing from 3 to 12 carbon atoms and from 3 to 10 hydroxyl groups, and mixtures thereof.

4. The process of claim 3 wherein the sugar surfactant is an alkyl and alkenyl oligoglycoside corresponding to formula (II) wherein $R_2$ alkyl and/or alkenyl radical containing from 12 to 14 carbon atoms and p is a number from 1 to 3.

5. The process of claim 1 wherein the negative temperature gradient is from 170° C. at the entrance opening of the evaporator to 20° C. at the exit opening of the evaporator.

6. The process of claim 1 wherein the anionic surfactant granules have a bulk density of from 550 to 650 g/l.

7. The process of claim 1 wherein the anionic surfactant granules have a mean particle size diameter of from 2.0 to 2.8 mm.

8. The process of claim 1 wherein the anionic surfactant granules contain less than 5% by weight of particles smaller than 200μm in diameter.

9. The process of claim 1 further comprising cooling the anionic surfactant granules emitted from the exit opening with ambient air to form cooled anionic surfactant granules.

10. The process of claim 9 wherein the cooled anionic surfactant granules are powdered with silica.

11. The product of the process of claim 1.
12. The product of the process of claim 2.
13. The product of the process of claim 3.
14. The product of the process of claim 4.
15. The product of the process of claim 5.
16. The product of the process of claim 6.
17. The product of the process of claim 7.
18. The product of the process of claim 8.
19. A powdered detergent containing the anionic surfactant granules of claim 1.
20. A bar soap containing the anionic surfactant granules of claim 1.

* * * * *